United States Patent [19]
Hess et al.

[11] Patent Number: 5,666,199
[45] Date of Patent: Sep. 9, 1997

[54] APPARATUS AND PROCESS FOR DETECTING THE PRESENCE OF GEL DEFECTS IN ORIENTED SHEETS OR FILMS BASED ON POLARIZATION DETECTION

[75] Inventors: Kevin J. Hess; Mark J. Dreiling; Edwin Boudreaux, Jr.; Ashish M. Sukhadia, all of Bartlesville, Okla.

[73] Assignee: Phillips Petroleum Company, Bartlesville, Okla.

[21] Appl. No.: 273,087

[22] Filed: Jul. 11, 1994

[51] Int. Cl.$^6$ .................. G01J 4/00; G01N 21/00
[52] U.S. Cl. .......... 356/364; 356/370; 356/430; 356/259; 250/559.09; 250/559.42; 250/559.45; 250/559.46
[58] Field of Search .................. 356/364–370, 356/430, 239; 250/262, 272

[56] References Cited

U.S. PATENT DOCUMENTS

| | | | |
|---|---|---|---|
| 1,988,169 | 1/1935 | Duckwall | 88/56 |
| 3,469,104 | 9/1969 | Hector | 250/219 |
| 3,812,348 | 5/1974 | Lippke | 250/561 |
| 3,890,221 | 6/1975 | Muehlethaler | 209/111.7 |
| 4,226,538 | 10/1980 | Van Beeck | 356/430 |
| 4,264,207 | 4/1981 | Batyrev et al. | 356/364 |
| 4,501,953 | 2/1985 | Hollinetz | 219/384 |
| 4,656,663 | 4/1987 | Jansson et al. | 382/8 |
| 4,684,487 | 8/1987 | Gawrisch | 356/364 |
| 4,692,799 | 9/1987 | Saitoh et al. | 358/106 |
| 4,972,091 | 11/1990 | Cielo et al. | 250/562 |
| 5,220,178 | 6/1993 | Dreiling et al. | 250/572 |

FOREIGN PATENT DOCUMENTS

| | | |
|---|---|---|
| 61-025042 | 2/1986 | Japan. |
| 04335145 | 11/1992 | Japan. |

*Primary Examiner*—Richard A. Rosenberger
*Assistant Examiner*—Jason D. Eisenberg
*Attorney, Agent, or Firm*—Ryan N. Cross

[57] ABSTRACT

A gel defect detection system for the optical inspection of defects in oriented transparent and translucent sheet. The system utilizes two polarizing filters with adjustable orientations so that the transmission axis is from about 70 degrees to about 110 degrees or from about 80 degrees to about 100 degrees. The system uses these polarization filters to help distinguish gel defects from the surrounding oriented sheet.

7 Claims, 2 Drawing Sheets

APPARATUS AND PROCESS FOR DETECTING THE PRESENCE OF GEL DEFECTS IN ORIENTED SHEETS OR FILMS BASED ON POLARIZATION DETECTION

BACKGROUND OF THE INVENTION

In one aspect the invention relates to a method and apparatus for detecting defects in a polymeric sheet or film. According to another aspect, the invention relates to a method and an apparatus for detecting defects in an oriented film.

In the past, defects in transparent and translucent polymeric sheets and films (hereinafter jointly referred to as sheets), have been detected by a visual inspection of the sheet. This visual inspection is a rather subjective test based on the laboratory technician's perceptions and, consequently, is prone to errors. Moreover, this visual inspection is mentally and physically fatiguing to the inspector, rendering it difficult to carry out continuous inspection operations. Therefore, there is a need to remove at least one source of human error from the detecting process by doing a computer aided count of defects.

In transparent and translucent polymeric sheets, typically polymer films, gel defects show up as thick spots in the sheets which can vary greatly in size. Most often they will appear transparent but a microscopic examination will indicate that they contain a gel or polymer particle at the core of the defect. Typically, these gel, or fisheye, defects will be comprised of small bits of plastic that were not completely melted before the formation of the sheet from the plastic. Because of their transparent or translucent nature, the gel defect can act to transmit light, thus, making them difficult to detect by prior detection methods which relied on the transmission of light through the sheet.

SUMMARY OF THE INVENTION

It is, therefore, an object of the present invention to provide an apparatus and method which produces reproducible data on the defects in a polymeric sheet of transparent or translucent material.

It is a further object of the present invention to provide an apparatus and method which can detect gel defects in an oriented film.

The above objects are realized in a method of inspecting a polymeric sheet comprising: placing at least a portion of the sheet between a first polarizing filter having a first transmission axis and a second polarizing filter having a second transmission axis wherein the first polarizing filter and the second polarizing filter are oriented such that the angle between the first transmission axis and the second transmission axis is greater than 0° and less than 180°; projecting a beam of light through the first polarizing filter, through the portion of the sheet and through the second polarizing filter; collecting the beam of light after it passes through the first polarizing filter, the portion of the sheet and the second polarizing filter; and analyzing the thus collected beam of light to detect defects in the portion of the sheet.

According to another aspect of the invention, there is provided an apparatus capable of detecting the presence of defects in a polymeric sheet comprising: a light source positioned on a first side of the sheet; a light analyzing means for receiving and analyzing light received from the light source, wherein the light analyzing means is positioned on a second side of the sheet and opposing the light source; a first polarizing filter having a first transmission axis, wherein the first polarizing filter is interposed between the light source and the sheet; and a second polarizing filter having a second transmission axis, wherein the second polarizing filter is interposed between the sheet and the light analyzing means and the first polarizing filter and the second polarizing filter are oriented so that the angle between the first transmission axis and the second transmission axis is greater than 0° and less than 180°.

BRIEF DESCRIPTION OF THE DRAWINGS

FIG. 2 does not include the shielding enclosure or any structural supports.

DETAILED DESCRIPTION OF THE INVENTION

Figure 1:
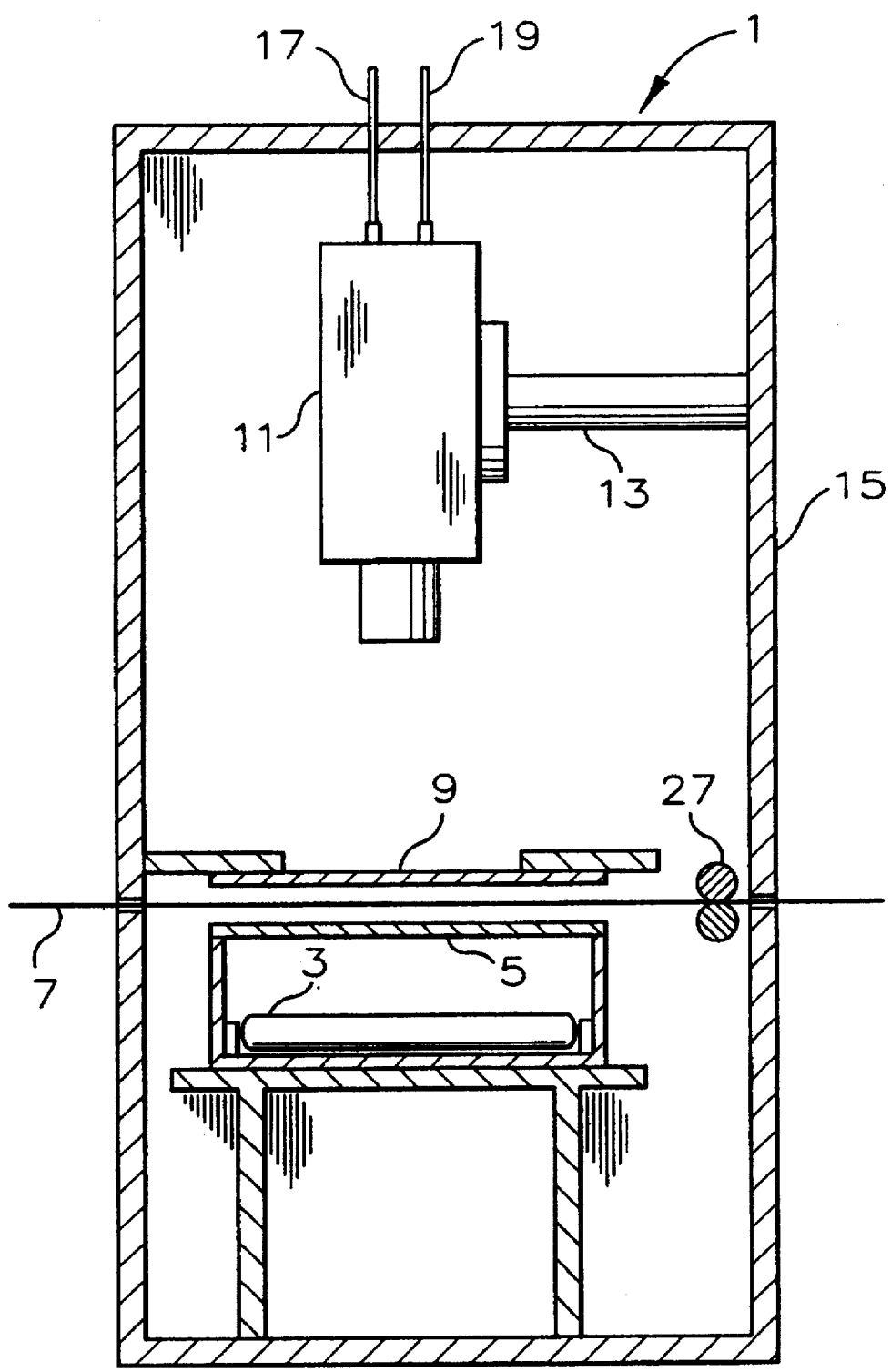
FIG. 1 is a plane view of a device according to the present invention with part of the shielding enclosure removed.

In the detection of defects, it has been discovered that advantage can be taken of the different optical properties of a transparent or translucent sheets and the defects contained therein. Referring now to FIG. 1, a defect detection system 1 is illustrated which utilizes these optical differences. In defect detection system 1, light from the light source 3 passes through a first polarizing filter 5. Next, the light passes through a transparent or translucent polymeric sheet 7 and then, through second polarizing filter 9. Light which passes through second polarizing filter 9 is then received into light detector 11, shown as a video camera, which is held in place by support bracket 13 which is in turn attached to shielding enclosure 15. Shielding enclosure 15, in addition to providing a base and support for the elements of defect detection system 1, also prevents background light from reaching light detector 11 and, thus, interfering with the detection of defects.

Figure 2:
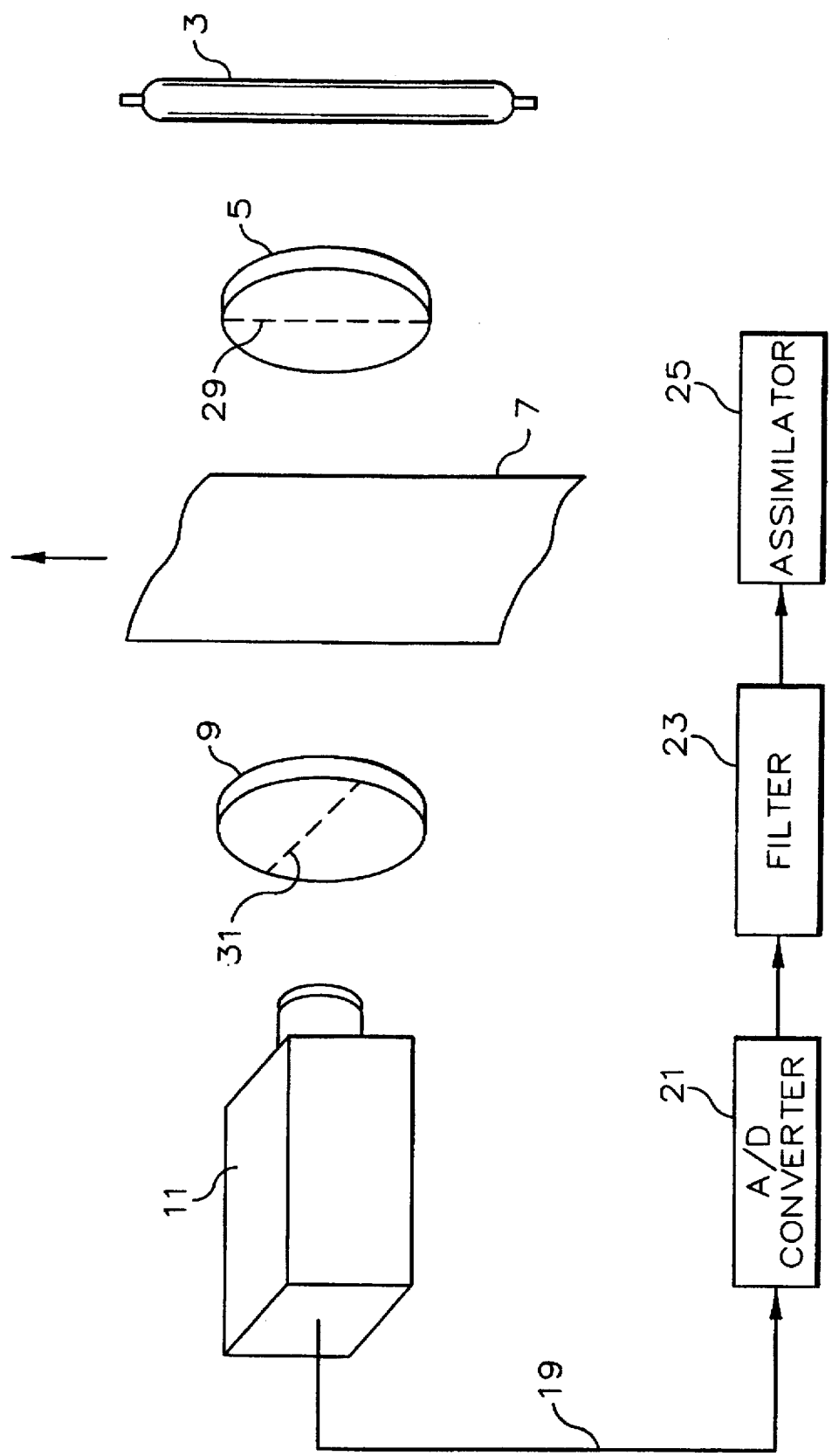
FIG. 2 is a schematic illustration of a device according to the invention.

Returning now to light detector 11, the light detector is provided power through the power supply cable 17 and provides an output signal through signal cable 19. As can better be seen from FIG. 2, signal cable 19 provides input to analog/digital converter 21, which in turn provides a digital signal to an electronic filter 23. The now filtered signal is then transmitted to assimilator 25 where information pertaining to the number and placement of the defects is assimilated. Typically, analog/digital converter 21, electronic filter 23 and assimilator 25 will be integral to a computer as subroutines and, therefore, the analog/digital conversion, filtering and assimilation will all be performed by the computer.

Although sheets can be manually placed between the polarizers for defect detection, generally, the sheets to be checked will be in the form of elongated films. Thus, defect detection system 1 is provided with automated rollers 27 which are in contact with sheet 7. Automated rollers 27 are turned by a motor (not shown) in order to advance the film, sheet 7, through the defect detection system 1 at a constant rate.

In operation, light from light source 3 passes through first polarizing filter 5 such that the light transmitted through first polarizer 5 will have an orientation parallel to a specific direction which is referred to as the transmission axis of the polarizing filter. The transmission axis of the first polarizing filter 5 can be seen in FIG. 2 as dotted line 29.

Next, the now oriented light passes through transparent or translucent polymeric sheet 7. The sheet can be made from any suitable material; however, the polymeric sheet should be transparent or translucent to allow the transmission of light. Preferably the material is made from polyethylene. Additionally, it is desirable that the polymeric sheet affects the light it transmits differently from how the defects contained within the polymeric sheet affect the light that they transmit. Therefore, preferably the polymeric sheet is an oriented sheet. By oriented sheet it is meant that during the production of the polymeric sheet, typically by extrusion or pultrusion, the majority of molecules that make up the particular sheet will have their major axes aligned so that they are substantially parallel. This will give the sheet at least a partial polarizing effect on light that is transmitted through it. Additionally, it is preferably than the defects to be detected be ones that transmit light, such as gel, or fisheye, defects. The defects should transmit the light so that it is scattered, so that it is rotated a different amount from any rotation caused by the polymeric sheet, or so that it is polarized in a different direction from any polarization caused by the polymeric sheet. Preferably the defects will scatter the light that they transmit.

After transmission of the light through polymeric sheet 7, the light will pass through second polarizing filter 9 which has transmission axis 31. Generally, it is desirable that the transmission axis 31 of second polarizing filter 9 and the transmission axis 29 of first polarizing filter 5 not be parallel, thus, the angle between the two transmission axes should be greater than 0° and less than 180°. It has been found however, that greater contrast between an oriented sheet and the defects contained therein can be produced by having an angle between the two transmission axes of from about 70° to about 110° and most preferably from about 80° to about 100°. While not wishing to be bound by theory it is believed that the greater contrast results because an oriented sheet will have at least a partial polarizing effect on the light while gel defects will have at least a partial scattering effect on the light.

After transmission through second polarizing filter 9, the light enters light detector 11 which generates a signal responsive to the thus collected beam of light. The signal is converted from analog to digital form, filtered, and analyzed for defects. As previously stated, typically, a computer will perform the analog/digital conversion, filtering and analysis; however, for convenience, the analog/digital conversion and filtering will be explained as occurring separate from the computer. The signal is sent to analog/digital converter 21 which digitizes the signal according to the number of pixels in the field of view of the light detection means to produce a digitized signal. The digitized signal is then sent to an electronic, or digital, filter 23, which can consist of a series of different electronic filters. Electronic filter 23 increases the contrast between the polymeric sheet and the defects contained therein and operates to reduce any resulting background noise contained in the digitized signal and adjusts the signal in comparison to a threshold value to create a binary signal. The signal from light detecting means 11 comprises data about the light value of each pixel within the field of view of light detecting means 11. Generally, each pixel will be represented as white, black, or some shade of gray there between; thus, for example, the light values of each pixel could be of any of 256 light values between and including white and black. After comparison with the threshold value, a binary signal is created which represents the polymeric sheet in terms of either black or white. From this binary signal assimilator 25 calculates the size, position of the defects contained in the polymeric sheet, the total number of defects and the average defect size.

A further understanding of the present invention and its advantages will be provided by reference to the following example. The example is provided merely to illustrate the practice of the invention and should not be read as limiting the scope of the invention or the appended claims in any way. Reasonable variations and modifications, not departing from the essence and spirit of the invention, are contemplated to be within the scope of the patent protection desired and sought.

EXAMPLE

A translucent sheet of 2.0 mil polyethylene film, marketed as Marlex® by Phillips Petroleum Company, 36 in. long and 4.5 in. wide, was analyzed for gel defects. The gel defect detector was set up for formal operation. The setup comprised a Sierra Scientific video camera interfaced to a Macintosh IIci computer using a SCION Corp. interface board. An Apple® video board was used to run an Apple® 13" RGB monitor. The camera was set up with the lens facing in a downward position approximately 5 in. away from the second polarizer and approximately 5.2 in. away from the light source.

Two Edmund Scientific Company polarizing filters were utilized. The polarizing filters were about 0.2 in. apart and had their transmission axes at about 80°. The film was placed between the two polarizers. The film was pulled through the defect detector by a pair of nip rollers driven by a stepper motor. The light source was a fluorescent light box utilizing two McMasters-Carr Supply Company fluorescent lamp bulbs, 6 watt, 9 in. fluorescent tube.

A public domain computer program called Image was used to collect and analyze data from the signal of the camera. Image is a computer program written in Pascal, a computer programming language, and is available on the National Institute of Health computer bulletin board. The version of Image used was version 1.37. The Image program was modified by adding a set of programmed commands to achieve remote control of the stepper motor which pulls the film sample through the apparatus. A command was written into the program which starts the motor. Another command was written into the program which stops the motor.

A feature of the Image computer program is a macro programming language. A macro programming language is a software routine which executes program commands by interpreting a text file. The text file specifies the commands to be executed. Thus, a macro containing the series of Image program commands necessary to filter and analyze the film samples were contained in a macro command. The macro command, when invoked, automatically executes the series of commands specified. For this example, a macro command was written to effect, in series, the registration and capture of an image by the digital video board, the digital filtering of the captured image to enhance contrast and reduce background noise, the analysis of the defects in the film, the compilation of the measurements in a tabular form documenting the size and location of each defect, the actuation of the stepper motor to advance the film sample, the stopping of the stepper motor, and the execution of the series of steps from image capture.

The Image software program also incorporates options for altering the video image fed from the camera. One such option inverts the image signal fed to the computer from the camera. By "invert" it is meant that the gray scale, as defined previously, is reversed. During normal operation the program registers the video image in 256 gray levels between white and black, with level 0 assigned to white and level 255 assigned to black. The reversed gray scale assigns level 0 to black and level 255 to white. For the purposes of this example, this option was enabled and the video input was inverted.

Additionally, the Image software program incorporates options in its particle analysis and counting routine. One of these options determined the minimum size and maximum size of defects to be included in the counting procedure. The "size" of a defect is defined as the total number of screen image pixels that are adjacent to one another. During the defect counting, the size of defects is reported in pixels. For the purposes of this example, the size range of defects which were counted was selected as 3 to 30 pixels.

Prior to operation of the detector, it was calibrated to obtain an average gray level in order to achieve a reproducible film grading. The average gray level is the average value of the gray levels of all the pixels in the image registered by the camera. The average gray level is referred to as the "background".

In order to calibrate the system the film to be analyzed was fed through the rollers and positioned between the polarizing filters. The light source was turned on to illuminate the film. The Image computer program was started. The calibration was done by adjusting the lens aperture to obtain a background gray level in the range of 150–190, as determined by the computer. This background level was found to give good results. It was assumed that there were no significant variations in the thickness of the test films.

After the detector was calibrated, the film was analyzed for gel defects using the detector. The macro command was executed. The series of procedures, as described previously, was executed. The image from the video camera was captured by the video board. The video camera collected visual data on an area slightly larger than 2 inch by 2 inch square (which equaled a 280 pixel wide and 280 pixel long plane). The captured image was cropped to 261×261 pixels square. The 261 pixel length corresponded to 2 inches, as determined by placing a scale under the camera in place of the film sample and calculating the pixels per inch scaling factor.

A series of digital filters were applied to the cropped image. Digital filters apply mathematical transforms to the pixels of the image in order to effect an enhancement of a desired attribute of the image.

The image was first filtered with a sharpening filter, the effect of which was to enhance the contrast between the defects in film and the rest of the film. A gradient filter was then applied to the image. This filter removes noise from the background of the image. Next, a threshold filter was applied to the image. A threshold filter reduces a gray scale image to a binary image. Thus a 256 gray level image is converted to a black and white image. The gray level at which the black to white transition occurs was set in the program. In this example, the threshold is set to 180. All features in the film with gray levels below 180 became black. By application of the series of filters as described here, the images of the defects in the film were enhanced and displayed as black specks against a white background. The defects, imaged as black specks, were then counted by the particle analysis routine of the program. The number pixels comprising each defect was counted and recorded. The x and y cartesian coordinates of the centroid of the defect were calculated and recorded. The number of pixels and cartesian coordinates of each defect are shown in table A. The cartesian coordinates were determined by placing the origin in the lower left corner of the captured image. Other information about the defects can be obtained by enabling options of the Image software program.

TABLE A

Defect Analysis Report for Example

| Defect No. | Area (pixels) | X coordinate (pixels) | Y coordinate (pixels) |
|---|---|---|---|
| 1 | 6.00 | 117.00 | 253.00 |
| 2 | 6.00 | 33.00 | 236.00 |
| 3 | 5.00 | 38.00 | 209.00 |
| 4 | 5.00 | 219.00 | 187.00 |
| 5 | 6.00 | 172.00 | 182.00 |
| 6 | 4.00 | 40.00 | 158.00 |
| 7 | 6.00 | 218.00 | 150.00 |
| 8 | 3.00 | 241.00 | 114.00 |
| 9 | 13.00 | 203.00 | 61.00 |
| 10 | 6.00 | 2.00 | 49.00 |
| 11 | 8.00 | 155.00 | 42.00 |
| 12 | 4.00 | 25.00 | 34.00 |
| 13 | 4.00 | 40.00 | 23.00 |
| 14 | 8.00 | 72.00 | 15.00 |

The average number of pixels in the detected defects was calculated and reported on the computer monitor. The results of the defect counting routine were tabulated and displayed on the computer monitor. The results correlated well with a visual inspection of the film. The Image software program compiled the tabulated data and created a software file containing the data which can be interpreted and displayed by other software programs.

That which is claimed:

1. A method of inspecting an oriented polyethylene sheet for gel defects comprising:
   (a) placing at least a portion of said sheet between a first polarizing filter having a first transmission axis and a second polarizing filter having a second transmission axis wherein there is an angle between said first transmission axis and said second transmission axis;
   (b) adjusting said first polarizing filter and said second polarizing filter so that they are oriented such that the angle between said first transmission axis and said second transmission axis is from about 70° to about 110° to create a contrast between said oriented polyethylene sheet and said gel defects;
   (c) projecting a beam of light through said first polarizing filter, through said portion of said sheet; and through said second polarizing filter;
   (d) collecting said beam of light after it passes through said first polarizing filter, said portion of said sheet and said second polarizing filter to obtain a thus collected beam; and
   (e) analyzing said thus collected beam of light to detect any said gel defects in said portion of said sheet.

2. A method according to claim 1 further comprising moving said sheet so that different portions of said sheet are inspected.

3. A method according to claim 1 further comprising shielding said steps (b) and (c) from light other than said beam of light.

4. A method according to claim 1 wherein said beam of light is collected in step (c) with a video camera having a field of view which generates a signal responsive to said thus collected beam of light and said signal is analyzed in step (d).

5. A method according to claim 4 wherein step (d) comprises digitizing said signal according to the number of pixels in the field of view of said video camera to produce a digitized signal, filtering said digitized signal electronically to increase the contrast between said defects and the rest of said portion of said sheet and to reduce any resulting background noise contained in said digitized signal to produce a filtered signal, adjusting said filtered signal in comparison to a threshold value to create a binary signal, and calculating the number of said defects and the position of each said defect from said binary signal.

6. A method of inspecting a moving oriented polyethylene film for gel defects comprising:

(a) passing said film between a first polarizing filter having a first transmission axis and a second polarizing filter having a second transmission axis wherein there is an angle between said first transmission axis and said second transmission axis;

(b) adjusting said first polarizing filter and said second polarizing filter so that they are oriented such that the angle between said first transmission axis and said second transmission axis is from about 80° to about 100° to create a contrast between said oriented polyethylene sheet and said gel defects;

(c) projecting a beam of light through said first polarizing filter and said second polarizing filter so that said beam of light passes through a portion of said film;

(d) collecting said beam of light after it passes through said first polarizer, said portion of said film, and said second polarizer to obtain a thus collected beam of light with a video camera which generates a signal responsive to said thus collected beam of light;

(e) digitizing said signal according to the number of pixels in the field of view of said camera to produce a digitized signal;

(f) filtering said digitized signal electronically to increase the contrast between said gel defects and the rest of said portion of said film and to reduce any resulting background noise contained in said digitized signal to produce a filtered signal;

(g) adjusting said filtered signal in comparison to a threshold value to create a binary signal; and (h) calculating the number of said gel defects and the position of each said defect from said binary signal.

7. An apparatus for detecting gel defects in a polymeric sheet comprising:

a light source positioned on a first side of said sheet;

a video camera for receiving light from said light source to obtain a thus received light and generating a signal responsive to said thus received light, wherein said video camera is positioned on a second side of said sheet and opposing said light source;

means for digitizing said signal according to the number of pixels in the field of view of said video camera to produce a digitized signal;

at least one electronic filter for filtering said digitized signal electronically to increase the contrast between said gel defects and the rest of said sheet and to reduce any resulting background noise contained in said digitized signal to produce a filtered signal;

means for adjusting said filtered signal in comparison to a threshold value to create a binary signal and for calculating the number of said gel defects and the position of each said gel defect from said binary signal;

a first polarizing filter having a first transmission axis, wherein said first polarizing filter is interposed between said light source and said sheet;

a second polarizing filter having a second transmission axis, wherein there is an angle between said first transmission axis and said second transmission axis, said second polarizing filter is interposed between said sheet and said light detecting means and said first polarizing filter and said second polarizing filter are oriented so that the angle between said first transmission axis and said second transmission axis is from about 80° to about 100°;

means for moving said sheet through said apparatus such that different portions of said sheet become interposed between said first polarizer and said second polarizer; and a shielding enclosure for enclosing said light source, said first polarizing filter, said second polarizing filter and at least a portion of said video camera so that only light from said light source is received by said video camera.

* * * * *